United States Patent [19]

Sweere

[11] Patent Number: 4,845,922
[45] Date of Patent: Jul. 11, 1989

[54] METHOD AND APPARATUS FOR FORMING AN ARTICLE HAVING A SECURELY-ATTACHED STRING

[75] Inventor: Douglas D. Sweere, Neenah, Wis.
[73] Assignee: Kimberly-Clark Corporation, Neenah, Wis.
[21] Appl. No.: 148,480
[22] Filed: Jan. 26, 1988

Related U.S. Application Data

[62] Division of Ser. No. 943,569, Dec. 18, 1988, Pat. No. 4,743,237.

[51] Int. Cl.[4] ................. B65B 9/06; B65B 61/14
[52] U.S. Cl. ...................... 53/413; 53/134; 53/451; 53/551
[58] Field of Search .............. 53/128, 133, 134, 135, 53/139, 410, 413, 414, 418, 428, 554, 451, 551, 552; 156/70, 204, 227, 474; 206/440, 616, 617, 618, 619; 383/8, 25, 28; 493/226, 909, 926

[56] References Cited

U.S. PATENT DOCUMENTS

| | | | |
|---|---|---|---|
| 1,557,032 | 10/1925 | Cooper | 53/413 |
| 1,731,665 | 10/1929 | Huebsch . | |
| 2,224,753 | 12/1940 | Yates | 53/418 X |
| 2,334,256 | 11/1943 | Eaton | 53/451 X |
| 2,335,159 | 11/1943 | Salfisberg | 493/226 X |
| 2,447,754 | 8/1948 | Hirschhorn | 53/413 |
| 2,496,609 | 2/1950 | Van Antwerpen | 156/581 X |
| 2,532,438 | 12/1950 | Behr . | |
| 2,710,007 | 6/1955 | Greiner et al. . | |
| 2,994,996 | 8/1961 | Klar | 53/134 |
| 3,024,788 | 3/1962 | Lane . | |
| 3,401,042 | 9/1968 | Frederick et al. | 53/413 |
| 3,483,801 | 12/1969 | Kupcikevicius | 493/226 X |
| 3,520,302 | 7/1970 | Jones | 128/285 |
| 3,736,935 | 6/1973 | Reimels | 128/296 |
| 3,794,024 | 2/1974 | Kokx et al. | 128/285 |
| 3,856,013 | 12/1974 | Dulle | 128/285 |
| 4,001,075 | 1/1977 | Menzner et al. | 156/581 |
| 4,027,673 | 6/1977 | Poncy et al. | 128/285 |
| 4,211,225 | 7/1980 | Sibalis | 128/285 |
| 4,328,804 | 5/1982 | Shimatani | 128/285 |
| 4,335,721 | 6/1982 | Matthews | 128/285 |
| 4,617,683 | 10/1986 | Christoff | 383/63 |
| 4,624,668 | 11/1986 | Siegers | 604/904 |
| 4,633,654 | 1/1987 | Sato et al. | 53/511 |
| 4,640,083 | 2/1987 | Takahashi et al. | 53/551 |
| 4,642,108 | 2/1987 | Sustmann | 604/379 |
| 4,743,237 | 5/1988 | Sweere | 604/358 |

FOREIGN PATENT DOCUMENTS 2423790 11/1975 Fed. Rep. of Germany .
3347649 11/1985 Fed. Rep. of Germany .

Primary Examiner—Robert L. Spruill
Assistant Examiner—Beth Bianca
Attorney, Agent, or Firm—Paul A. Leipold; Thomas J. Connelly

[57] ABSTRACT

A method and apparatus is disclosed for forming an article such as a tampon having a securely attached string. The method includes intermittently feeding filler members into one end of a hollow tube which is open at both ends. A sheet of heat sealable material is advanced towards the tube and folded so as to cylindrically wrap about the tube. The abutting edges of the material are fused together to form a cylindrical casing into which the filler members enter upon exiting the tube. Apertures are then transversely formed in the casing between the adjacent filler members and a string is inserted through the apertures. The casing is then heated and compressed against the string to form a permanent bond. After the bond is formed, the casing is severed to form individual articles which are sealed at both ends and have a string attached to one of the ends.

13 Claims, 4 Drawing Sheets

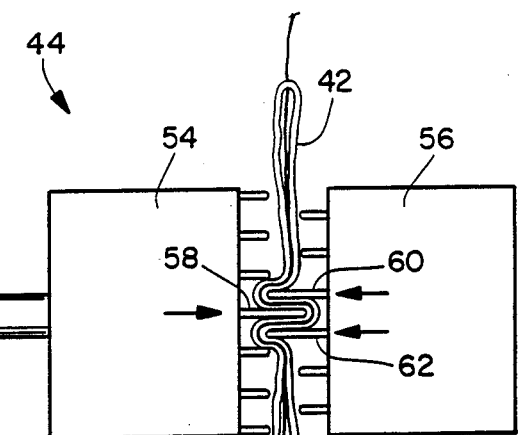
FIG. 2
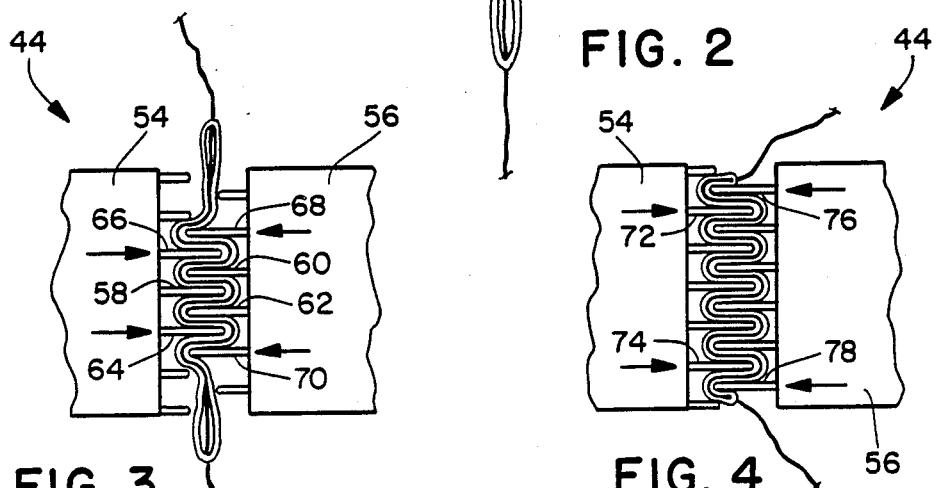
FIG. 3
FIG. 4
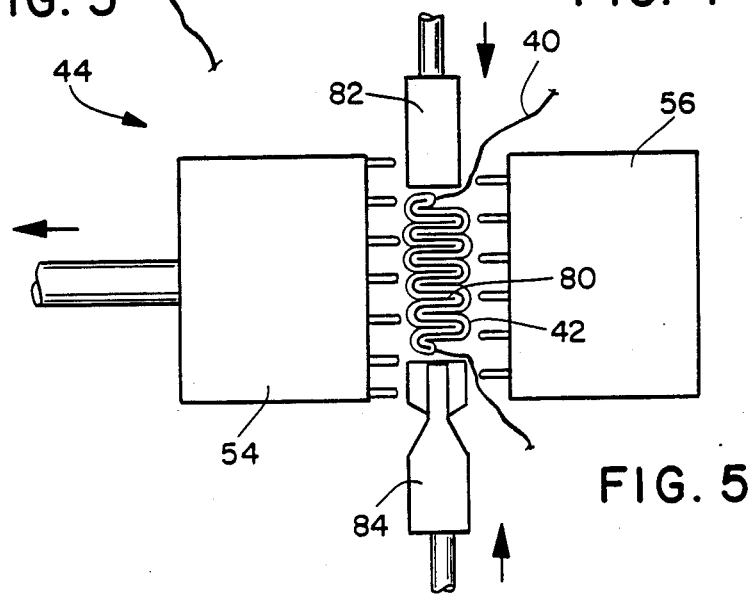
FIG. 5

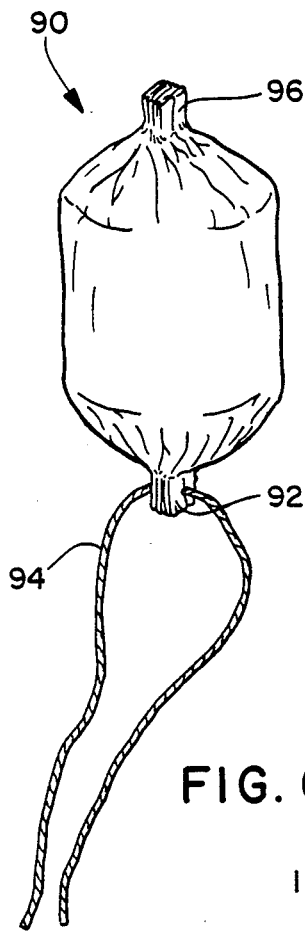
FIG. 6
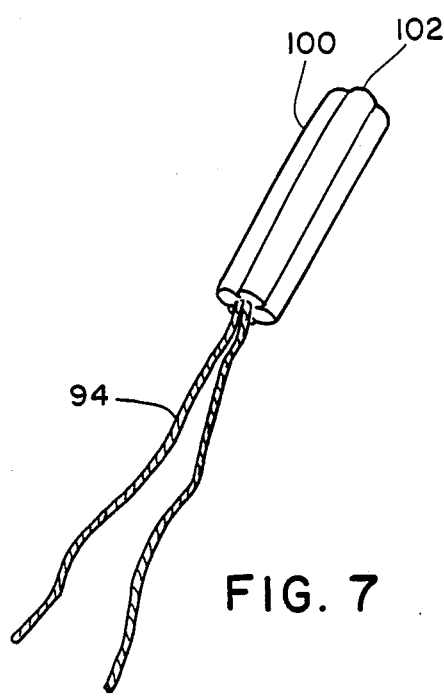
FIG. 7
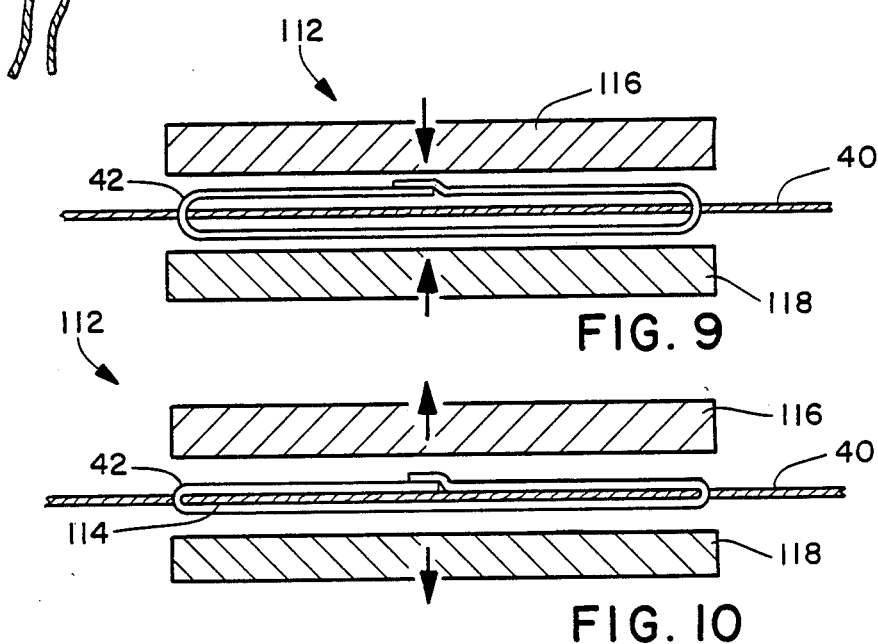
FIG. 9
FIG. 10

METHOD AND APPARATUS FOR FORMING AN ARTICLE HAVING A SECURELY-ATTACHED STRING

This is a divisional of co-pending application Ser. No. 943,569 filed on Dec. 18, 1988 now U.S. Pat. No. 4,743,237.

FIELD OF THE INVENTION

This invention relates generally to a method of forming a container having a securely-attached handling cord. It particularly relates to the formation of tampons having a thermoplastic gauze outer wrapping with the withdrawal cord thermoplastically bonded to the guaze.

BACKGROUND OF THE INVENTION

Intervaginal tampons are in common use by women for the retention of fluid or menses discharged along the walls of the vagina during the mestrual cycle. Such tampons are usually formed of absorbent material such as cotton, rayon, cellulose wadding, synthetic sponge, cellulose fluff, synthetic fibers or combinations of these materials compressed or molded usually to a generally cylindrical configuration of a size to fit within the vaginal tract.

Intervaginal tampons may be inserted by use of applicators which eject the tampons within the vagina, by stick insertion or by digital insertion. Tampons are generally provided with a withdrawal cord or string that is utilized to withdraw the tampon from the vagina. The attachment of the string to the tampon is critical in that it is necessary that the string be attached in such a manner that the tampon is withdrawn from the vagina in one piece. Further, the string or withdrawal cord must be attached in such a manner that it is not susceptible to becoming unattached from the tampon such that the tampon may be easily removed from the vagina.

Methods of attachment of the withdrawal cord to tampon shave included passing a string through the tampon and knotting the string after it has passed through the tampon. However, this system is subject to failure if the knot is not perfectly formed or becomes untied. It has been proposed in U.S. Pat. No. 1,731,665 —Huebsch and U.S. Pat. No. 2,710,007 —Greiner et al. that the gauze overwrapping of a tampon be extended and utilized as a withdrawal cord. A disadvantage of this system is that the gauze overwrapping material is more expensive than a cord and further, forms a larger withdrawal device that is not preferred by women. Further, the gauze covering, in addition to being thicker, has more of a tendency to wick fluid, which is undesirable in a tampon withdrawal cord.

Therefore, there remains a need for a method of quickly attaching a withdrawal cord to a tampon in such a manner that it will not come loose under any conditions.

SUMMARY OF THE INVENTION

A general object of this invention is to provide a method and apparatus for forming an improved tampon having a filler wrapped in a thermoplastic gauze and having a withdrawal cord bonded to the gauze.

Another object of this invention is to provide an efficient, low-cost method and apparatus for forming tampons with securely-attached cords.

A further object of this invention is to form a tampon having a heat-sealable gauze outer wrapping securely bonded to a handling cord.

Other objects and advantages of the present invention will become more apparent to those skilled in the art upon reading the following description.

These and other objects are generally accomplished by providing a method and apparatus to wrap a filler material with a porous gauze. The gauze material is thermoplastic and is heat sealed around the filler material. A string or cord is pierced through the gauze wrapping in a location exterior to the filler. The sides of the gauze wrapping are then brought together to surround the cord and heat and pressure are applied to fuse the cord to the gauze wrapping.

In a preferred form of the invention, the filler material is an absorbent for a tampon. After the fusing of the cord to the gauze wrapping, the tampon is compressed to the size conventionally utilized for a tampon and may be utilized either in a digital, stick or applicator-type tampon.

BRIEF DESCRIPTION OF THE DRAWINGS

FIGS. 2-5 illustrate the apparatus for fusing the cord to the wrapper.

FIG. 6 is a view of a container of the invention.

FIG. 7 is a view of a tampon of the invention.

FIGS. 9 and 10 are cross-sectional views of alternate apparatus for fusing the cord to the wrapper.

DETAILED DESCRIPTION OF THE PREFERRED EMBODIMENTS

The invention has many advantages over presently available tampons and the methods and apparatuses used for forming such tampons. One advantage of the present invention is that the withdrawal string will not come loose from the tampon. A second advantage is that the fastening of the withdrawal string to the outer gauze wrapping of the tampon is simple, low cost and reliable as heat and pressure are all that is required.

Figure 1:
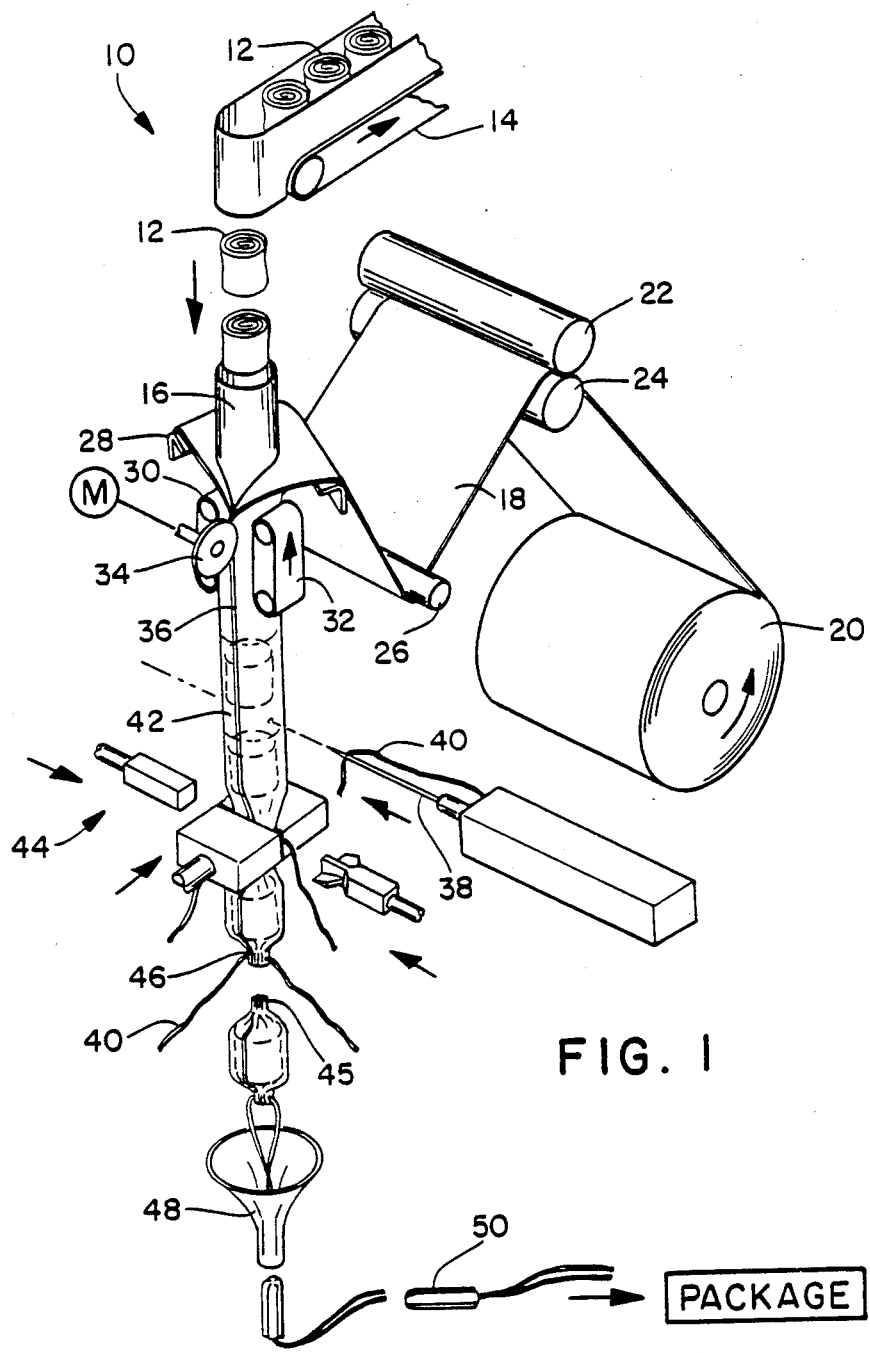
FIG. 1 is a perspective view of an apparatus and method for performing the invention.

Referring to FIG. 1, an apparatus 10 is shown for performing the method of producing tampons. Filler members 12 are intermittently fed by a conveyor 14 to the apparatus 10. The filler members 12 are rolled absorbent members which are dropped into a feed tube 16. Around the feed tube 16 there is wrapped a gauze material 18 that is supplied from a supply roll 20. The gauze material 18 passes between feed rolls 22 and 24 and under feed roll 26 so that its tension is controlled. The gauze material 18 passes over a folding member 28 that aids in wrapping the gauze 18 around the feed tube 16. The gauze material 18, forming the outer wrapper, is moved by belt apparatuses 30 and 32. The gauze material 18 is moved downward, as illustrated in FIG. 1, as the belt apparatuses 30 and 32 rotate and press the gauze 18 against the feed tube 16. A heat sealing wheel 34 fuses the edges of the gauze material 18 together on a line 36. As the absorbent fillers 12 exit the feed tube 16, after being wrapped with the gauze material 18, the gauze material 18 forms a cylindrical casing 42 which is pierced by a reciprocating needle 38 carrying a string or cord 40. The cord 40 is supplied from a source of continuous cord (not shown) and is cut off by a cutter (not shown) after piercing through the cylindrical casing 42.

The reciprocating needle 38 pierces the casing 42 between adjacent filler members 12 and the cord 40 is cut off such that it freely hangs on each side of the cylindrical casing 42. After the cylindrical casing 42 is pierced by the cord 40 it moves to a heat sealing and cutting unit 44 where both the casing 42 and the cord 40 are compressed and sealed together. The compressed seal is cut into a cord bearing lower seal 46 and a cord-free upper seal 45 by the sealing unit 44 and then exits therefrom. The casing 42 then enters a compression device 48 where it is compressed to form a compressed tampon 50. The tampon 50 may then be packaged for shipping and sale.

FIGS. 2–5 show the sealing and cutting apparatus 44 in greater detail. In the sealing of the upper and lower seals 45 and 46, respectively, of the tampon 50, an accordion-like fold 80 is first formed. Heat sealing anvils 54 and 56 are used having interlocking pins 58, 60, 62, 64, 66, 68, 70, 72, 74, 76 and 78. As shown in FIG. 2, it is necessary that the centermost pins 58, 60 and 62 be extended when the anvils 54 and 56 are first brought towards each other in order to gather the extra gauze material 18 necessary to form the fan fold 80 formed between the pin 58 of the anvil 54 and the pins 60 and 62 of the anvil 56. Then sequentially, as best shown in FIG. 3, the next outermost pins 64 and 66 of the anvil 54 and the pins 68 and 70 of the anvil 56 are brought together. Lastly, as best shown in FIG. 4, the moveable pins 72 and 74 of the anvil 54 and the moveable pins 76 and 78 of the anvil 56 are brought into contact. After the fan-folded seal 80 is formed, see FIG. 5, it is compressed and cut by heated anvils 82 and 84 to further seal the withdrawal cord 40 into the casing 42.

FIG. 6 illustrates a container 90 that is sealed at one end by a seal 92 which has a cord 94 integrally, thermally bonded. The container 90 also has an upper seal 96. This upper seal 96, is formed by severing a larger seal, formed in the sealing and cutting apparatus 44, into the cord containing lower seal 46 and the opposite seal 45. The container 90 may represent a tampon prior to compression to form a pledget. The container 90 may also be utilized as a container for absorption of spills or as a container for food materials such as tea.

FIG. 7 illustrates a tampon 100 having an attached withdrawal cord 94 and a forward end 102 formed by compression of the container 90 The tampon 100 may be utilized in a tube-type tampon applicator. If designed for use with a stick or digitally, the forward end 102 would be rounded for easier insertion.

Figure 8:
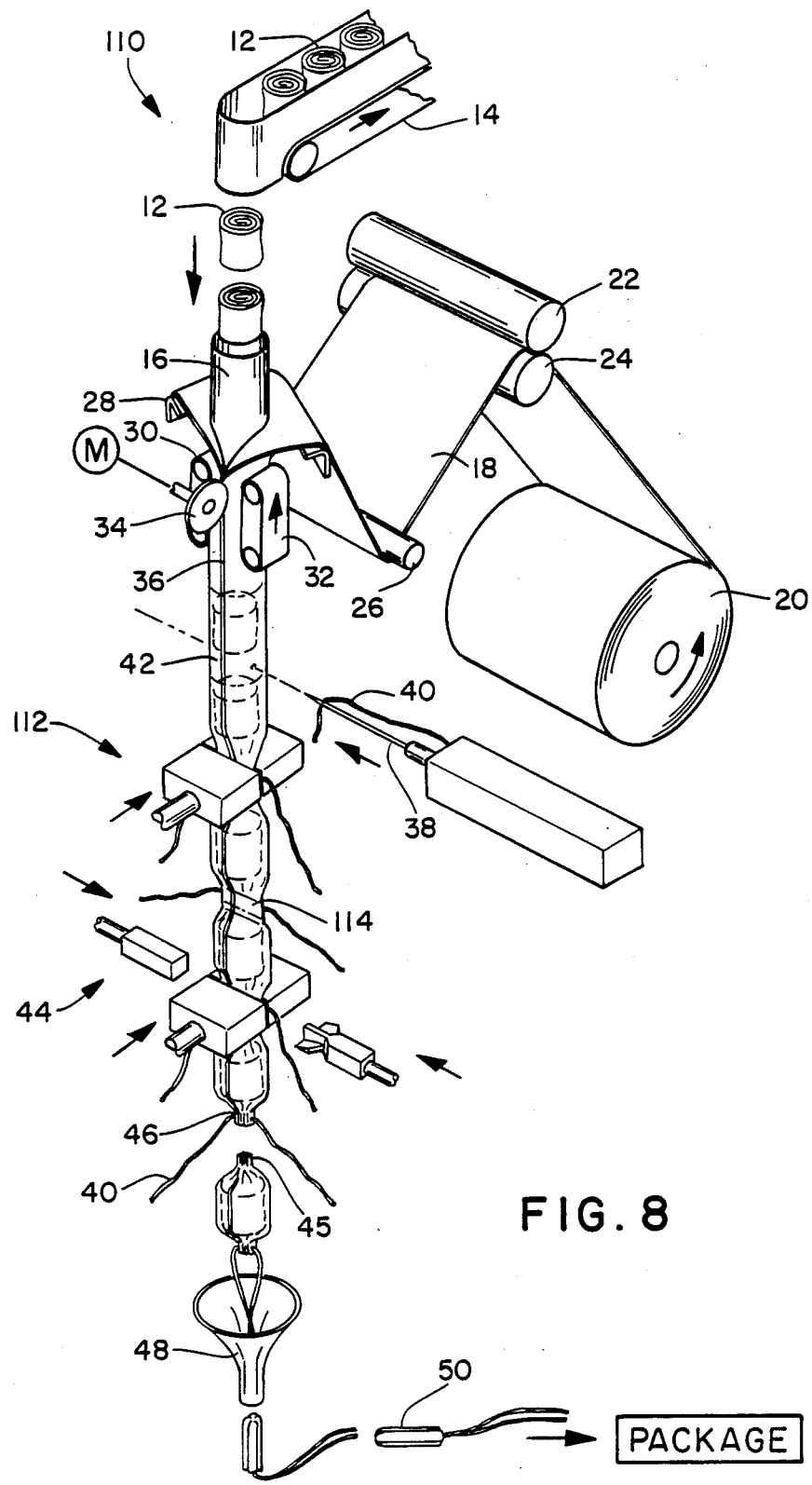
FIG. 8 is a perspective view of an alternate method and apparatus for performing the invention.

FIG. 8 shows an alternate apparatus 110 which corresponds to the apparatus 10, shown in FIG. 1, except that another fusing section 112 has been added. The fusing section 112, located before the heat sealing and cutting unit 44, provides a seal 114 that first seals the casing 42 to the cord 40. The seal 114 is then fan folded, fused and cut in the unit 44. It would also be possible to cut the seal 114 in the unit 44 and not fan fold if a somewhat larger, less secure cord seal was satisfactory.

FIGS. 9 and 10 illustrate the compression and fusing of the casing 42 and the cord 40 in the fusing section 112. In FIG. 9, the casing 42 is compressed about the cord 40 by heated anvils 116 and 118 and fused to the cord 40. In FIG. 10, the anvils 116 and 118 are shown being separated after forming the seal 114.

While the invention has been described with a continuous formation, it could also be utilized to seal and provide cords for individual bags formed of a thermoplastic material. Furthermore, there are other apparatuses that can be utilized for compression and heat sealing of the withdrawal cords to the thermoplastic outer wrapping. For instance, the seal could be formed without a fan fold.

The withdrawal cord 94 may be formed of any suitable material. Typical of such materials are cotton as well as polymer materials such as rayon, polypropylene, polyester, nylon or blends thereof. The withdrawal cord 94 is less likely to wick fluid if treated with wax or silicone. However, cotton, rayon and polyester are the preferred materials as they are low in price, soft and strong. The term cord as used herein is intended to include groups of fibers, such as twisted cotton, as well as single polymer cords.

The gauze material 18 forming the outer wrapping of the container may be any thermoplastic permeable material. Typical of such materials are perforated thermoplastic films and thermoplastic polymer netting materials. Preferred materials have been found to be thermoplastic spunbonded materials, particularly polypropylene spunbonded materials, as they are permeable, low in cost and fuse at lower temperatures. Furthermore, such materials have previously been found suitable for covers for tampons.

The filler material 12 may be any material that is desired and to which a material handling cord can be attached. Typical of such filler materials utilized in tampons are polypropylene, cellulose acetate, nylon, acrylic and carboxymethylcellulose. Other suitable materials include cotton linters, rayon and mixtures of these fibers. Any fiber that is able to be compressed for shaping into a smaller size for formation into a tampon pledget and that will expand when wet is suitable. The fiber may be folded or rolled prior to being compressed.

The attachment of the withdrawal cord 40 or 94 to the container is even more secure if a thermoplastic cord is utilized that has a fusion temperature somewhat near that of the gauze material 18. The withdrawal cord may be formed of a polypropylene material that will have a compatible fusion temperature with the preferred polypropylene spunbonded cover material.

The tampons formed by the instant invention may be utilized in cardboard or plastic applicators that are inserted into the vagina prior to the tampon pledget being expelled from the applicator. The tampons further may be formed into stick tampons or be digitally insertable tampons.

The method of compressing a package having a withdrawal string attached thereto into a tampon pledget are well known. The method generally includes the use of molds that compress the package to the desired shaped tampon pledget. It is beneficial if the handling of the tampon pledget in entering and leaving such molds is by the withdrawal cord. This will automatically eliminate defective products in which the cord has been severed in the molding operation or in another manufacturing process. Packaging means for tampons are also known in the art and conventional equipment may be utilized. Likewise, the tampons may be packaged by hand if desired.

While the formation of the tampons have been described using a continuous process involving the sealing of a casing 42 at both ends in order to enclose the filler material 12, it is possible that a preformed bag which is open at one end could be utilized. The material handling cord could then pass through the open end of the bag which is later sealed by heat and compression.

While the container with the material handling cord has been set forth in the preferred embodiment as a tampon, it is also possible that the method and apparatus of this invention could be utilized to form other products such as teabags, sachets of odor-releasing compounds or potpourris of such materials. These and other uses are intended to be included within the spirit and scope of the appended claims.

While the invention has been described in connection with specific embodiments, it will be understood that the invention is not intended to be limited to those embodiments. On the contrary, the invention is intended to encompass all alternative, modifications and variations as may be included within the spirit and scope of the appended claims.

I claim:

1. A method of forming an article having a securely attached string, said method comprises the steps of:
   (a) intermittently feeding filler members into one end of a hollow tube which is open at both ends;
   (b) advancing a sheet of heat sealable material toward said tube and folding said material about the outside of said tube to form a casing having abutting edges aligned approximately parallel to the longitudinal axis of said casing;
   (c) fusing said abutting edges together to form a cylindrical casing into which said filler member enter upon existing said tube;
   (d) forming apertures transversely through said casing between said adjacent filler members and inserting a string through said apertures;
   (e) heating and compressing said casing against said string to form permanent bonds therebetween; and
   (f) severing said casing at said permanent bonds to obtain individual articles which are sealed at both ends and have a string attached to one of said ends.

2. The method of claim 1 wherein said heat-sealable material is a thermoplastic.

3. The method of claim 2 wherein said thermoplastic is spunbonded polypropylene.

4. The method of claim 1 wherein said heat-sealable material is a heat fusible gauze.

5. The method of claim 1 wherein said filler members comprise an absorbent.

6. The method of claim 1 wherein said casing is heated and compressed between at least three interlocking pins to form a fan folded bond with said string.

7. A method of forming a tampon having a securely-attached withdrawal string, said method comprising the steps of:
   (a) intermittently feeding absorbent members into one end of a hollow tube which is open at both ends;
   (b) advancing a sheet of heat-sealable material toward said tube and folding said material about the outside of said tube to form a casing having abutting edges aligned approximately parallel to the longitudinal axis of said casing;
   (c) fusing said abutting edges together to form a cylindrical casing into which said absorbent members enters upon exiting said tube;
   (d) forming apertures transversely through said casing between adjacent absorbent members and inserting a string through said apertures;
   (e) heating and comprising said casing against said string to form permanent bonds therebetween;
   (f) severing said casing at said permanent bonds to obtain individual tampon preforms which are sealed at both ends and have a string attached to one of said ends; and
   (g) compressing said tampon preforms to form finished tampons.

8. An apparatus for forming a tampon having a withdrawal string integrally bonded thereto, said apparatus comprising:
   (a) supply means for intermittently feeding absorbent members into one of a hollow tube which is open at both ends;
   (b) means for advancing a sheet of heat-sealable material toward said tube and folding said material about the outside of said tube to form a casing having abutting edges aligned approximately parallel to the longitudinal axis of said casing;
   (c) means for joining said abutting edges together to form a cylindrical casing into which said absorbent members enter upon existing said tube;
   (d) means for forming apertures transversely through said casing between said adjacent absorbent members and means for inserting a string through said apertures;
   (e) means for heating and compressing said casing against said string to form permanent bond therebetween;
   (f) cutting means for severing said casing at said permanent bonds to obtain tampon preforms which are sealed at both ends and have a withdrawal string attached to an end thereof; and
   (g) compression means for reducing the size of each of said tampon preform into a finished tampon.

9. The apparatus of claim 8 wherein said means for aperturing said casing and inserting a string is a reciprocating needle.

10. The apparatus of claim 8 including means for fan folding said permanent bonds before said casing is severed into individual tampon preforms.

11. The apparatus of claim 10 wherein said fan folding means includes a pair of moveable anvils having a plurality of interlocking pins.

12. The apparatus of claim 8 wherein said means for heating and compressing said casing physically bonds said casing to itself as well as to said string.

13. An apparatus for forming a tampon having a withdrawal string integrally bonded thereto, said apparatus comprising:
   (a) supply means for intermittingly feeding absorbent members into one end of a hollow tube which is open at both ends;
   (b) means for advancing a sheet of heat-sealable material toward said tube and folding said material about the outside of said tube to form a casing having abutting edges aligned approximately parallel to the longitudinal axis of said casing;
   (c) means for joining said abutting edges together to form a cylindrical casing into which said absorbent members enter upon exiting said tube;
   (d) means for forming apertures transversely through said casing between said adjacent absorbent members and means for inserting a string through said apertures;
   (e) means for heating and compressing said casing against said string to form permanent bonds therebetween;
   (f) means for fan folding said permanent bonds;
   (g) cutting means for severing said casing at said permanent bonds to obtain tampon preforms which are sealed at both ends and have a withdrawal string attached to an end thereof; and
   (h) compression means for reducing the size of each of said tampon preform into a finished tampon.

* * * * *